(12) United States Patent
Akagami et al.

(10) Patent No.: US 8,283,120 B2
(45) Date of Patent: Oct. 9, 2012

(54) NONCONTACT STIRRING METHOD, NONCONTACT STIRRING APPARATUS, METHOD AND APPARATUS FOR REACTING NUCLEIC ACID HYBRIDIZATION USING THE APPARATUS, METHOD FOR DETECTING NUCLEIC ACID IN SAMPLE, APPARATUS FOR DETECTING NUCLEIC ACID, METHOD FOR DETECTING ANTIBODY IN SAMPLE, APPARATUS FOR DETECTING ANTIBODY

(75) Inventors: Yoichi Akagami, Akita (JP); Masami Kagaya, Akita (JP)

(73) Assignee: Governor of Akita prefecture, Akita-shi (JP)

( * ) Notice: Subject to any disclaimer, the term of this patent is extended or adjusted under 35 U.S.C. 154(b) by 254 days.

(21) Appl. No.: 12/604,640

(22) Filed: Oct. 23, 2009

(65) Prior Publication Data

US 2010/0173300 A1    Jul. 8, 2010

(30) Foreign Application Priority Data

Oct. 23, 2008  (JP) ................................. 2008-272991
Oct. 22, 2009  (JP) ................................. 2009-243468

(51) Int. Cl.
*C12Q 1/68* (2006.01)
*G01N 33/53* (2006.01)
*B01F 11/00* (2006.01)
*B28C 5/48* (2006.01)

(52) U.S. Cl. .......................... 435/6.11; 435/7.1; 366/108
(58) Field of Classification Search ............... 435/6, 6.1, 435/6.11, 7, 7.1; 366/108
See application file for complete search history.

(56) References Cited

OTHER PUBLICATIONS

Liu et al, Lab on a Chip, vol. 2, pp. 151-157 (2002).*

* cited by examiner

*Primary Examiner* — Robert T. Crow
(74) *Attorney, Agent, or Firm* — Oblon, Spivak, McClelland, Maier & Neustadt, L.L.P.

(57) ABSTRACT

A noncontact stirring method, a noncontact stirring apparatus, a method and apparatus for reacting nucleic acid hybridization using the apparatus, a method for detecting nucleic acid in a sample, an apparatus for detecting nucleic acid, a method for detecting antibodies in a sample, and an apparatus for detecting antibodies in minute droplets 1 μmL or less in an electric field are proposed that can be utilized to speed up biodetection processes, hybridization processes in DNA analysis, ELISA antigen fixing processes, blocking processes, antibody-antigen reaction processes and color reaction processes; and pathogen identification, CRP tests, methods of propagating cells or bacilli such as colon bacilli in a liquid culture medium, and chemical analyses.

4 Claims, 10 Drawing Sheets

FIG.4

1xSYBR Green 1-based detection result and analysis result of XX DNA used as sample Conventional method (Shaker-stirred for 10 minutes at 46°C)

x-type probe    X-type probe

Analysis result

| | Non-specific | Specific |
|---|---|---|
| Red | 135 | 170 |
| Green | 183 | 172 |
| Blue | 0 | 0 |

Green brightness difference |specific - Non-Specific|=11

From the small difference between non-specific and specific brightness, it can be determined that stirring is not proceeding normally.

Electric field noncontact stirring method 5 minutes at 46°C
32 Hz, 2.6 kV, offset 1.7 kV x-type probe    X-type probe

| | Non-specific | Specific |
|---|---|---|
| Red | 153 | 191 |
| Green | 195 | 236 |
| Blue | 0 | 4 |

Green brightness difference |specific - Non-Specific|=41

Good fluorescence emission is observed, so it can be determined that stirring was good.

FIG.5

Schematic diagram of electric field noncontact stirring apparatus

ELISA analysis process time results

| Antigen:333 μg/mL | Conventional method | With electric field noncontact stirring method |
|---|---|---|
| Antigen and antibody amounts | Antibody :1.1 μg/mL | Antibody :1.1 μg/mL |
| ① Antigen fixing | 25°C  60 minutes | 25°C  10 minutes |
| ② Washing | 20 minutes | 0.5 minutes |
| ③ Blocking | 30 minutes | 15 minutes |
| ④ Washing | 20 minutes | 0.5 minutes |
| ⑤ Antigen-antibody reaction | 30 minutes | 15 minutes |
| ⑥ Washing | 20 minutes | 0.5 minutes |
| ⑦ Color observation | 30 minutes | 15 minutes |
| Total | 210 minutes | 56.5 minutes |

//

NONCONTACT STIRRING METHOD, NONCONTACT STIRRING APPARATUS, METHOD AND APPARATUS FOR REACTING NUCLEIC ACID HYBRIDIZATION USING THE APPARATUS, METHOD FOR DETECTING NUCLEIC ACID IN SAMPLE, APPARATUS FOR DETECTING NUCLEIC ACID, METHOD FOR DETECTING ANTIBODY IN SAMPLE, APPARATUS FOR DETECTING ANTIBODY

BACKGROUND OF THE INVENTION

1. Field of the Invention

The present invention relates to a noncontact stirring method, a noncontact stirring apparatus, a method and apparatus for reacting nucleic acid hybridization using the apparatus, a method for detecting nucleic acid in a sample, an apparatus for detecting nucleic acid, a method for detecting antibodies in a sample (ELISA reaction), and an apparatus for detecting antibodies (ELISA reaction apparatus) in droplets of 1 mL or less in a high-voltage alternating-current electric field, particularly minute microliter-order droplets that can be utilized to speed up biodetection processes and hybridization processes in genetic analysis, ELISA (Enzyme-Linked ImmunoSorbent Assay: used to detect and quantify the concentration of antibodies or antigens in a sample) antigen fixing processes, blocking processes, antibody-antigen reaction processes and color reaction processes, in pathogen identification, CRP tests (C-Reactive Protein: examining for the presence or absence of protein in looking for inflammation, infection or tissue damage), and methods of propagating cells or bacilli such as colon bacilli in a liquid culture medium.

2. Description of the Prior Art

In genetic analysis, ELISA antigen fixing processes, blocking processes, antigen-antibody reaction processes and color reaction processes, pathogen identification, CRP tests, biodetection and other such chemical analysis processes, having the reactions take place while the sample solution is stirred takes a lot of time, so there is a need to speed this up for the future of tailor-made medicine.

Industrially, analysis and quantification of various biological components such as cells, sugar, protein and nucleic acid are conducted on a routine basis in a wide range of tests, such as clinical tests, food tests and environmental tests. In the field of clinical tests in particular, the diagnosis of diseases, the determining of the efficacy of treatments, and the measurement of antibodies are done by analyzing and quantifying specific biological components in bodily fluids such as blood, urine and the like. Utilizing the interaction of DNA (deoxyribonucleic acid) and intercalators, antigen fixing reactions based on hydrophobic bonding, antigen-antibody reactions, and electrophoresis utilizing the physicochemical properties of the target substance are methods in general use for analyzing and quantifying biological components. However, depending on what the target biological component is, the reactions and operation of these methods may take up much time and lack precision, and in terms of principle are limited and may not provide accurate analysis.

For example, in the case of a nucleic acid hybridization process in genetic analysis that uses static reactions, the reaction time is long, in the order of 60 minutes to 6 hours. If a shaker is to be used for stirring, the liquid amount must be at least 1 mL, and a specific time is required for the solution to reach the optimum temperature, making it difficult to speed up the process. Attempts have been made to reduce the time taken to reach the optimum temperature by reducing the liquid amount of the solution to 1 mL or less, and in particular to a minute amount in the microliter-order, in addition to which the minute amount of solution is vigorously stirred internally, to thereby improve the speed of the hybridization reaction.

Because in a nucleic acid hybridization reaction it is considered that the types of molecules that form pairs are chain molecules, the reaction cannot be completed by a single collision, the formation of a continuous chain pairing reaction proceeding through a plurality of molecular collisions. That is, the reaction time can be greatly reduced by using stirring for mutual collision.

For example, in an immune reaction in an ELISA, at each step generally a liquid amount of 50 μL to 100 μL has to be left static for 30 minutes to 1 hour, so the whole process requires around 4 hours. The reaction proceeds by molecular diffusion. Therefore, it is possible to greatly reduce the reaction time by reducing the amount of the solution and by stirring it.

As described in the above, in order to improve reaction speed using a solution amount of 1 mL or less, and in particular a minute microliter-order amount, to expedite obtaining a high-quality outcome, there is a need for a noncontact stirring technology that does not use rotors or stirring elements.

As noncontact stirring technology that has already been proposed, there are known commercial shakers that impart shaking (undulating motion) to a solution, a method that blows air bubbles onto the surface of the solution, a method that imparts ultrasonic waves, and so forth.

SUMMARY OF THE INVENTION

However, although the above shakers impart an undulatory motion to a solution contained in a cylinder, cell or flask so that, in a relatively large amount of solution, the stirring effect can be expected to be correspondingly large, in the case of a solution amount of 1 mL or less, and in particular a minute microliter-order amount, an adequate stirring effect is either not observed or the reactions require a very long time. That is, in the case of minute solution amounts, it is known that under gravity the surface tension of droplets from a reaction dominates, making it difficult to stir the interior of the droplets.

With a method of blowing air bubbles onto the surface of the solution in which the stirring effect is imparted to the surface of the liquid, an adequate stirring effect inside the liquid is not observed.

Furthermore, with the method of stirring with the application of ultrasonic waves, molecular motion is promoted by projecting ultrasonic waves at 20 to 40 kHz, raising the frequency of molecular collisions and making the nucleic acid hybridization relatively faster, providing a corresponding observable stirring effect. However, the temperature of the liquid is raised by the cavitation of the ultrasonic stirring, causing the problem that temperature-dependent reactions such as hybridization do not take place. Also, when stirring based on ultrasonic cavitation technology is applied to a solution amount of 1 mL or less, and in particular, to a minute microliter-order amount, there is the problem that the minute droplets are instantly dispersed, making stirring impossible. There have also been cases of DNA being damaged by molecular collisions. Another problem is that of noise produced in cases in which ultrasound of around 20 kHz is used.

An object of the present invention is to propose a method of noncontact stirring of a minute amount of 1 mL or less, and in particular of minute microliter-order droplets, that i) can reduce reaction time in, for example, nucleic acid hybridization processes in genetic analysis, ELISA antigen fixing processes, blocking processes, antibody-antigen reaction processes and color reaction processes, and in pathogen identification and CRP tests, without giving rise to any of the aforementioned problems, and can rise the precision of analysis and have high reproducibility by improving analysis sensitivity.

The present invention was proposed in view of the foregoing and, based on assiduous studies that focused on the phenomenon of droplet absorption caused by the Coulomb force of a high-voltage alternating-current electric field, which is a physical means, which was found to be applicable to noncontact stirring of droplets of 1 mL or less, and in particular of minute microliter-order droplets, and that by applying an external electric field could greatly reduce the reaction times even in the nucleic acid hybridization processes of genetic analysis, and ELISA antigen fixing processes and antibody-antigen reaction processes.

Specifically, when a 10 μL droplet of sterile ultrapure water containing calcium carbonate (for observation, having a particle diameter of 50 nm and a concentration of 0.05%) was dripped onto a plastic substrate and subjected to the plus side of a 0.5 kV/mm, 0.1 Hz square wave voltage waveform, the surface of the droplet quivered but no stirring of the contents occurred. Then, when the frequency of the applied electric field was increased, observation of the droplet confirmed a good stirring phenomenon at 85 Hz to 95 Hz.

The following are the conditions under which a mixture of sample DNA and hybridization solution was stirred. 10 μL of the solution was dripped on a plastic substrate (because at or below 30° C. the solution becomes more viscous and solidifies, heating and humidification states were observed. Also, since the viscosity of the droplet is high compared to water, the droplet has a low response frequency. Good stirring of the droplet at 30 to 40 Hz was confirmed.) and a high-voltage alternating-current electric field was applied to effect a noncontact stirring state for five minutes of hybridization. This was followed by an analysis, which provided a clear result. SSC buffer (sodium citrate and sodium chloride) and SDS (sodium lauryl sulfate) were used for the hybridization solution.

The following are the conditions under which an antigen solution and an antibody solution were stirred. First, 1 μL of the antigen solution was dripped onto a polystyrene or other such plastic substrate (since the viscosity of the antigen solution and antibody solution is high compared to water, the solutions have a low response frequency. Good stirring of the droplets at 200 Hz was confirmed.), and the reaction was carried out using electric field noncontact stirring technology for 10 minutes at room temperature and maintained humidity. After washing, blocking, which using a conventional method requires 30 minutes, was completed in 15 minutes using electric field noncontact stirring technology at room temperature and maintained humidity. Next, 1 μL of the antibody solution was dripped down and the reaction was carried out using electric field noncontact stirring technology for 15 minutes at room temperature and maintained humidity, and after washing, was reacted with a chromogenic substrate. Analysis showed stable color development. BSA (333 μg/mL of bovine serum albumin in PBS) was used for the antigen solution. 1% egg albumin in PBS was used for the blocking solution. 1.1 μg/mL HRP labeled anti-BSA antibody in 1% egg albumin was used for the antibody solution. Implemented on a chromogenic substrate using 3 mM ABTS in 0.1% $H_2O_2$ in a 0.1 M citric acid buffer of pH 4.0.

That is, the present invention relates to a noncontact stirring method and a noncontact stirring apparatus that under a humidity environment of 60±10%, repetitively generates square waves with a plus-side bias having a plus-side main applied voltage of 0.35 to 2.5 kV/mm to which is added an offset voltage of 0.2 to 2.2 kV/mm which, by also applying 2 to 40 frequency bundles of frequency 0.1 to 800 Hz, varies electric field waves of a high-voltage alternating-current electric field applied noncontactively to minute droplets of 1 mL or less (preferably in the order of microliters).

The present invention also proposes a method for reacting nucleic acid hybridization that uses said electric field noncontact stirring method, comprising reacting nucleic acid having an RNA or DNA complementary sequence.

The present invention also proposes a method for detecting nucleic acid in a sample that uses said electric field noncontact stirring method, comprising reacting nucleic acid having an RNA or DNA complementary sequence and measuring the reaction products that are produced.

The present invention also proposes a method for detecting antibodies in a sample (ELISA reaction) that uses said electric field noncontact stirring method, comprising fixing a protein to a plastic substrate and effecting an antigen-antibody reaction that reacts protein having a property of binding specifically to said protein.

As an apparatus for implementing the above nucleic acid hybridization reaction, the present invention also proposes an apparatus for reacting nucleic acid hybridization, comprising parallel plate electrodes, a plastic probe DNA immobilization substrate, a heater temperature control apparatus, a humidity-maintained, heat-insulated sealed vessel, a set of apparatuses that generates an electric field for stirring comprising a function generator that generates a fundamental waveform, a high-voltage amplifier that amplifies the signal (gain×1000), and an oscilloscope whereby the applied waveform is observed, the electric field being supplied to the parallel plate electrodes by connecting the plus terminal of the electric field supplied from the high-voltage amplifier to the lower parallel plate electrode and connecting the earth side to the upper parallel plate electrode.

As an apparatus for implementing the above method for detecting nucleic acid in a sample, the present invention also proposes an apparatus for detecting nucleic acid, comprising parallel plate electrodes, a plastic probe DNA immobilization substrate, a heater temperature control apparatus, a humidity-maintained, heat-insulated sealed vessel, a set of apparatuses that generates an electric field for stirring comprising a function generator that generates a fundamental waveform, a high-voltage amplifier that amplifies the signal, and an oscilloscope whereby the applied waveform is observed, the electric field being supplied to the parallel plate electrodes by connecting the plus terminal of the electric field supplied from the high-voltage amplifier to the lower parallel plate electrode and connecting the earth side to the upper parallel plate electrode.

As an apparatus for implementing the above method for detecting antibodies in a sample, the present invention also proposes an apparatus (ELISA reaction apparatus) for detecting antibodies (ELISA reaction), comprising parallel plate electrodes, a plastic antigen immobilization substrate, a humidity-maintained, heat-insulated sealed vessel, a set of apparatuses that apply an electric field for stirring comprising a function generator that generates a fundamental waveform, a high-voltage amplifier that amplifies the signal (gain× 1000), and an oscilloscope whereby the applied waveform is observed, the electric field being supplied to the parallel plate electrodes by connecting the plus terminal of the electric field supplied from the high-voltage amplifier to the lower parallel plate electrode and connecting the earth side to the upper parallel plate electrode.

By enabling noncontact stirring inside minute amounts of solution by applying Coulomb force generated by a high-voltage alternating-current electric field to droplets of 1 mL or less, and particularly to minute microliter-order solution droplets, the present invention can be used to speed up processes in various industrial fields such as, for example, biodetection processes, nucleic acid hybridization in genetic analysis, ELISA antigen fixing processes, blocking processes, antigen-antibody reaction processes and color reaction processes, pathogen identification, CRP tests, chemical analysis, propagation of cells or bacilli such as colon bacilli in liquid culture medium, and so forth.

For example, compared to the aforementioned shaking method that is the conventional noncontact stirring method, the stirring time can be reduced to around one-fifth.

Also, since the electric field noncontact stirring method of the invention does not use rotors or stirring elements, results are obtained that clearly show it is difficult for contamination to occur, process time is decreased and variation is suppressed. Another advantage is that it does not generate the noise of conventional ultrasonic stirring.

Moreover, it can be applied to solid-liquid reactions and liquid-liquid reactions, the stirring conditions can be readily controlled by an external electric field, and as the apparatus has a simple configuration, it can readily be made smaller. Also, the motion of the liquid and the degree of progress of color reactions can be confirmed at the same time if transparent electrodes are used. In addition, stirring is possible under various temperature, humidity, vacuum and gas environments.

Also, the method of the present invention for reacting nucleic acid hybridization reacts RNA or DNA and nucleic acid having an RNA or DNA complementary sequence while using a high-voltage alternating-current electric field to apply a Coulomb force, and applies the noncontact stirring method to the hybridization reaction.

The method of the present invention for reacting nucleic acid hybridization can be used to expeditiously effect hybridization using a smaller amount of DNA than that used by the above conventional ultrasonic stirring. Reducing the amount of DNA that is handled enables the PCR protocol to be shortened. That is because the process of raising and lowering the temperature becomes simpler. That is, developing technology for the noncontact stirring of droplets of 1 mL or less, and in particular of minute microliter-order droplets, by the application of a high-voltage alternating-current electric field, and applying it to the hybridization that is a genetic analysis process, improves reaction efficiency and reduces reaction time. Speedy and highly reliable analysis results can be further obtained by also applying a high-voltage alternating-current electric field and noncontact stirring during intercalation.

Thus, in addition to the intermittently external application of a high-voltage alternating-current electric field in the order of 0.1 to 800 Hz reducing the reaction time, it enables hybridization to be effected with a smaller amount of DNA, giving it a very high practical value.

Also, the ELISA method of the present invention applies the Coulomb force of a high-voltage alternating-current electric field while promoting the reaction of an antigen and an antibody specific to the antigen, and applies the above electric field noncontact stirring method for minute droplets to the antigen fixing reaction and antigen-antibody reaction.

Also, the ELISA method of the present invention enables the antigen fixing reaction and antigen-antibody reaction to be expeditiously effected with a solution amount that is smaller than that of the above conventional static method.

Thus, in addition to the intermittently external application of a high-voltage alternating-current electric field in the order of 0.1 to 800 Hz reducing the reaction time, it enables the antigen fixing reaction and antigen-antibody reaction to be effected using a reaction liquid amount of 1 mL or less, and in particular, a microliter-order reaction liquid amount, giving it a very high practical value.

With the method of the invention for detecting nucleic acid in a sample, after hybridization, reaction products that are produced are measured, enabling the detection of nucleic acid in the sample. The method has high reproducibility and can raise the precision of an analysis.

It can therefore be utilized in fields such as clinical tests, food tests and environmental tests.

DESCRIPTION OF THE PREFERRED EMBODIMENTS

The present invention enables noncontact stirring inside droplets of 1 mL or less, and particularly in minute microliter-order droplets, by applying Coulomb force generated by a high-voltage alternating-current electric field to the droplets. Specifically, under a humidity environment of 60±10%, square waves with a plus-side bias are repetitively generated having a plus-side main applied voltage of 0.35 to 2.5 kV/mm to which is added an offset voltage of 0.2 to 2.25 kV/mm, and 2 to 40 frequency bundles (composing burst waveforms) of frequency 0.1 to 800 Hz are also applied, varying the electric field waves of a high-voltage alternating-current electric field applied noncontactively, to minute droplets of 1 mL or less (preferably in the order of microliters).

Electrical discharge can occur if the electric field strength (kV/mm) on the plus side is more than 2.5 kV/mm, and stirring will not take place if it is lower than 0.35 kV/mm.

Also, electrical discharge can occur if the offset voltage is more than 2.25 kV/mm, and stirring will not take place if it is lower than 0.2 kV/mm.

Figure 2:
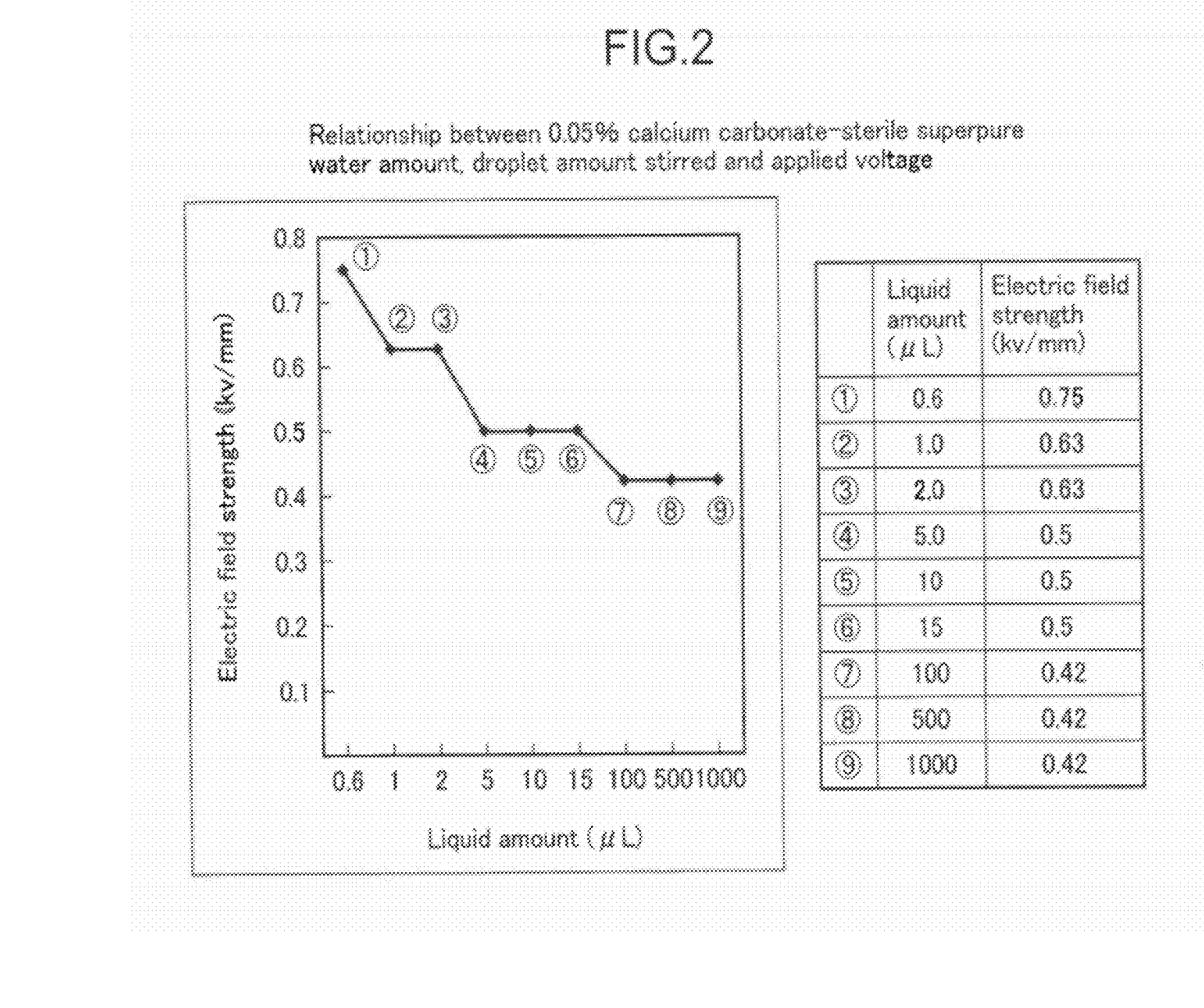
FIG. 2 A graph showing the relationship between the calcium carbonate-sterile superpure water amount and the electric field strength (kV/mm) generated by the stirring described below.
Figure 3:
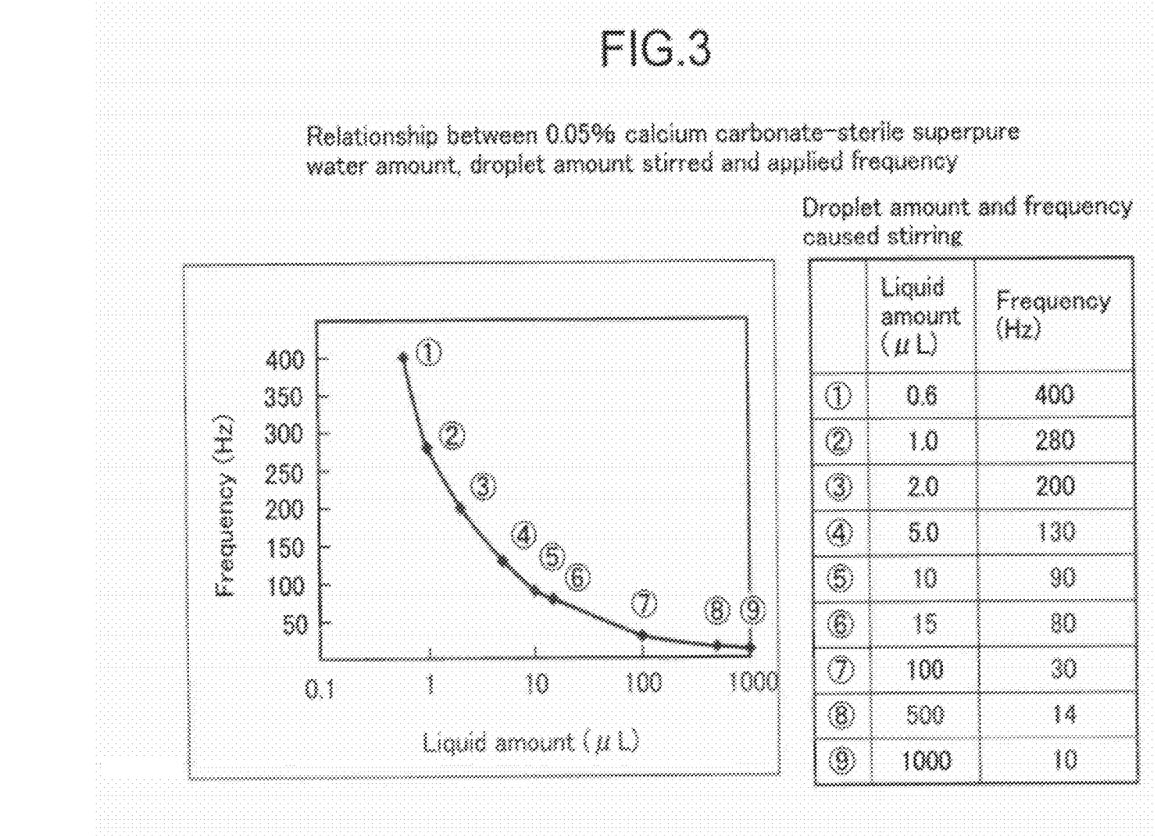
FIG. 3 A graph showing the relationship between the calcium carbonate-sterile superpure water amount and the applied frequency generated by the stirring described below.

Moreover, the influence that electric field strength and frequency have on the stirring effect is dependent on the droplet amount. FIG. 2 and FIG. 3 show this relationship between electric field strength and liquid amount, and frequency and liquid amount.

The present invention also proposes a method for reacting nucleic acid hybridization that utilizes the above electric field noncontact stirring method in the hybridization reaction. That is, it reacts nucleic acid having an RNA or DNA complementary sequence, while applying the Coulomb force generated by a high-voltage alternating-current electric field.

The present invention also proposes an ELISA method that utilizes the above electric field noncontact stirring method in the antigen fixing reaction and antigen-antibody reaction. That is, the antigen can be efficiently affixed to the substrate and the antigen and specific antibody reaction expeditiously accomplished while the Coulomb force generated by the high-voltage alternating-current electric field is applied.

RNA that can be used in this invention includes pronucleus, eukaryotic, and virus-derived mRNA.

DNA that can be used in this invention includes, pronucleus, and eukaryote-derived chromosome DNA, organella-derived mitochondrial DNA, chloroplastic DNA, virus chromosome and plasmid DNA, etc.

Labeling substances that can be used include fluorescent dye, radioactive isotope (32P, 32P, 35S, etc.), substances that can bind with detectable substances, such as biotin, as well as alkaline phosphatase, peroxidase, and β-galactosidase and the like.

RNA and DNA binding proteins include double-chain DNA binding proteins that regulate gene expression by altering the DNA structure (for example, lambda phage cro protein, cI repressor, and lactose operon repressor), single-chain DNA binding proteins that are essential for replication, recombination and repair processes (for example, SSB found in organisms ranging from colon bacilli to higher forms of life), proteins that bind strongly to chromosomes, helping to maintain the higher-order structure of the chromosomes (for example, histone and non-histone proteins), DNA-dependent ATPase such as helicase (for example, replication protein such as rep helicase, n' or dnaB, and recombination protein such as recA and recB), and topoisomerase that provides DNA conformational change (for example, topoisomerase I and II, lambda phage int protein, and φX174 gene A protein). The high-voltage alternating-current electric field application conditions are the same as those used in the above-described nucleic acid hybridization reaction.

In the method of the invention for reacting nucleic acid hybridization, first, the hybridization solution containing a nucleic acid having an RNA or DNA complementary sequence is dripped onto a plastic substrate on which RNA or DNA is affixed, and the substrate is inserted between parallel plate electrodes. These are then placed in a humidity-maintained, heat-insulated sealed vessel, and subjected to the Coulomb force of a high-voltage alternating-current electric field. The high-voltage alternating-current electric field application conditions can be applied to intercalation as well as hybridization.

The apparatus for implementing the nucleic acid hybridization reaction is as follows. The probe DNA immobilization plastic substrate onto which the reaction solution is dripped is inserted between the parallel plate electrodes. A heater with a temperature control apparatus is disposed at the bottom of the electrode, and these are placed in the humidity-maintained, heat-insulated sealed vessel. The high-voltage alternating-current electric field that is applied to the parallel plate electrodes comprises a function generator that generates a fundamental wave, a high-voltage amplifier (gain×1000), and an oscilloscope for observing the applied waveform. The +side of the high-voltage amplifier is connected to the lower electrode and the earth is connected to the upper electrode, applying the high-voltage alternating-current electric field to the parallel plate electrodes.

As described in the above, the present invention enables the hybridization to be expeditiously effected using an amount of DNA that is smaller than that used by the ultrasonic stirring method. The concentration of the DNA used in this invention is 15 ng/μL or more, in the order of 20 ng/μL. The hybridization liquid amount is 0.5 μL to 10 μL/DNA spot. Conventional ultrasonic stirring uses 113 ng/μL of lambda DNA, an amount that is about five times more than the amount used by the present invention (a liquid amount of at least several tens of microliters).

From this, it can be inferred that with the above ultrasonic stirring, the processing amount (the liquid amount of solution used) is increased to keep down the effect on the DNA. With the present invention, the Coulomb force of a high-voltage alternating-current electric field is applied to minute droplets of 1 mL or less, and in particular to minute microliter-order droplets, but it is difficult to apply ultrasonic stirring to such small droplets.

The present invention also proposes a method for detecting nucleic acid in a sample by reacting complementary RNA or DNA with RNA or DNA in the sample while applying the Coulomb force of a high-voltage alternating-current electric field, and measuring the reaction products that are produced. This utilizes the property of hybridization of DNA or RNA (DNA probe or RNA probe) and DNA or RNA having a complementary sequence. The high-voltage alternating-current electric field application conditions are the same as those used in the method of reacting nucleic acid hybridization in which the reaction with the above RNA or DNA and RNA or DNA complementary nucleic acid is effected while applying a high-voltage alternating-current electric field.

Also, as a method utilizing the hybridization reaction of the present invention, during probe manufacture enzymatic reaction can be used to detach the phosphate group at the end of the nucleic acid, and the isotope-labeled phosphate group is bound. In this enzymatic reaction, the high-voltage alternating-current electric field may be applied externally. The high-voltage alternating-current electric field application conditions are the same as the above.

In the reaction of fixing the antigen to the substrate and the antigen-antibody reaction in an ELISA, the present invention also proposes a method for detecting an antibody in a sample by effecting the reactions while applying the Coulomb force of a high-voltage alternating-current electric field and then measuring the reaction products that are produced. This utilizes the hydrophobic property of the function group of the antigen to bind electrostatically to the substrate, and the antigen property of binding specifically to the antibody.

The high-voltage alternating-current electric field application conditions are the same as those used in the ELISA method in which the antigen fixing reaction is effected while applying a high-voltage alternating-current electric field to the antigen and a specific antibody.

With the ELISA method of the present invention, blocking is carried out after fixing the antigen. In this blocking process too, the high-voltage alternating-current electric field may be applied externally. The high-voltage alternating-current electric field application conditions are the same as the above-described conditions.

With the ELISA method of the present invention, also, during antibody measurement, enzymatic reaction is utilized for color development of the chromogenic substrate. In this color reaction too, the high-voltage alternating-current electric field may be applied externally. The high-voltage alternating-current electric field application conditions are the same as the above-described conditions.

Figure 1:
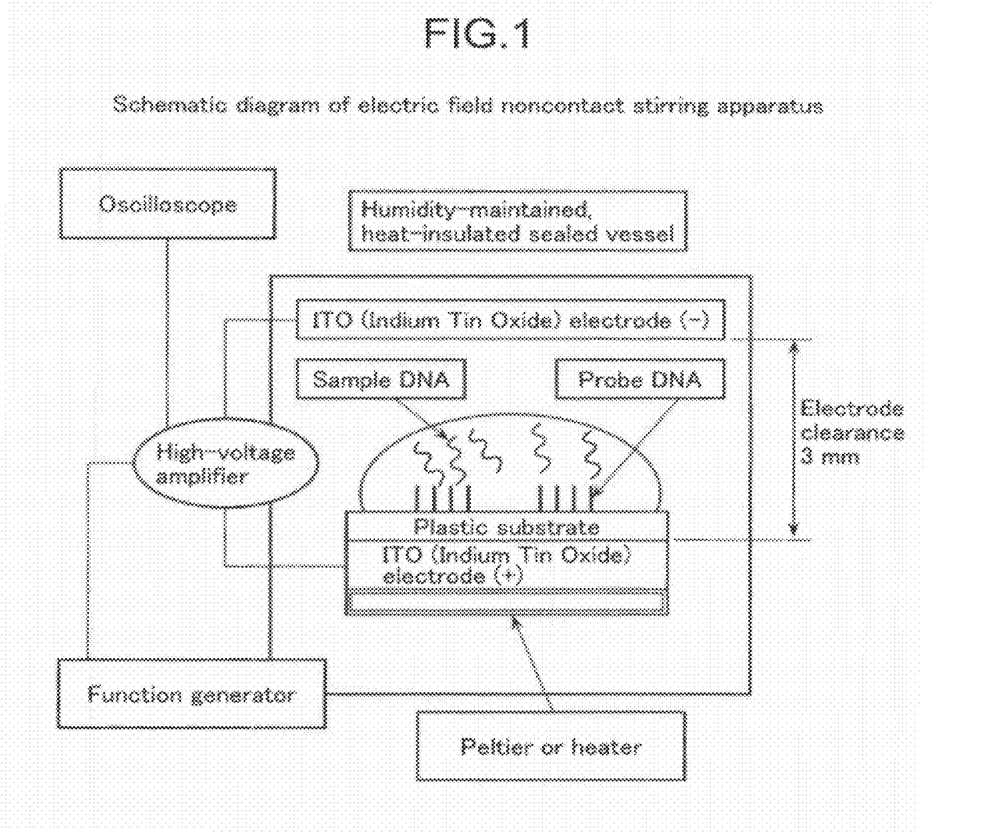
FIG. 1 A cross-sectional drawing showing an outline of the electric field noncontact stirring apparatus used in Example Experiment 1, Example Experiment 2 and Example Experiment 3.

With respect to the principle shown in FIG. 1, since it is possible for water to be drawn in by the plus electric field, the electric field is applied as a repetitive waveform on the plus side, and is biased to oscillate the wavefront of the minute droplets. A gentle oscillation can be supplied to the droplet wavefront by switching the waveform On and Off in bundle cycles of from about 2 to 20, thereby stirring the contents.

In the hybridization reaction of the present invention, first, DNA having a sequence complementary to the sample DNA is immobilized on a plastic substrate, onto which a mixture of the sample DNA and the hybridization solution is dripped. It is desirable that this be done at an ambient temperature of 43 to 47° C. and a humidity of 60±10%. The DNA immobilization substrate is inserted between the parallel plate electrodes (the bottom one being the plus electrode), and the high-voltage alternating-current electric field is applied under the same conditions as those described in the above. The application time is 5 minutes.

In the ELISA method of the present invention, the high-voltage alternating-current electric field is applied, under the same conditions as those described in the above, when the antigen is fixed to the plastic substrate, and when the antigen is reacted with a specific antibody. The application time is 10 minutes in the case of the antigen fixing process, and 15 minutes in the case of the antigen-antibody reaction process. It is desirable that this be done at an ambient temperature of 25±2° C., and a humidity of 60±10%.

Another example is that of a suspension culture. To prevent cells becoming implanted, the concentration of calcium ions in the culture is lowered, that of phosphate ions is raised, and the cells are stirred by a magnetic stirrer. A feature is that the suspension culture can be used to produce many cells in a culture solution having a fixed capacity.

In the suspension culture, cells can be cultured with high efficiency by using the noncontact stirring phenomenon by applying the high-voltage alternating-current electric field of this invention.

Another example is that of pathogen identification. This normally requires about 5 hours to determine the presence or absence of agglutination. The pathogen identification time can be reduced by using the electric field noncontact stirring technology of the invention during the agglutination time.

Another example is that of CRP tests, in which the presence or absence of inflammation or tissue destruction is determined by measuring the turbidity of CRP, which is a diagnostic indicator. The time for measuring the turbidity can be reduced by using the electric field noncontact stirring technology of the invention during the reaction.

Methods of utilizing the electric field noncontact stirring technology of the present invention include promoting reactions during intercalation following the hybridization, promoting ELISA blocking process reactions and color development reactions, pathogen identification, CRP tests, cell cultures, and reducing the PCR reaction time. This makes it applicable to a wide range of industrial fields such as clinical tests, food tests and environmental tests.

The strength (kV/mm) of the applied electric field is optimized according to the liquid amount of the sample.

When a droplet of sterile ultrapure water containing calcium carbonate (for observation, having a particle diameter of 50 nm and a concentration of 0.05%) was dripped onto a plastic substrate and the movement under an electric field between parallel plate electrodes observed, it was confirmed that calcium carbonate particles in the droplet moved vigorously in the case of 0.6 μL at 0.75 kV/mm (4 mm between electrodes), 1 to 2 μL at 0.63 kV/mm (4 mm between electrodes), 5 to 15 μL at 0.5 kV/mm (4 mm between electrodes), and 100 to 1000 μL at 0.42 kV/mm (7 mm between electrodes).

These results are shown in the graph of FIG. 2.

The frequency of the applied electric field is optimized according to the liquid amount of the sample.

When a 10 μL droplet of sterile ultrapure water containing calcium carbonate (for observation, having a particle diameter of 50 nm and a concentration of 0.05%) was dripped onto a plastic substrate and the movement under an electric field between parallel plate electrodes observed, it was confirmed that calcium carbonate particles in the droplet moved vigorously in the case of 0.6 μL at 380 to 420 Hz, 1 μL at 260 to 310 Hz, 2 μL at 195 to 220 Hz, 5 μL at 125 to 140 Hz, 10 μL at 85 to 95 Hz, 15 μL at 70 to 85 Hz, 100 μL at 30 Hz, 500 μL at 13 to 15 Hz, and 1000 μL at 10 Hz. These results are shown in the graph of FIG. 3.

[Hybridization Example]

First, the probe DNA was fixed to a plastic substrate and a mixture of the sample DNA and the hybridization solution was dripped thereon, and this was inserted between parallel plate electrodes having a clearance of 4 mm. A function generator was used to set the electric field fundamental voltage, waveform and frequency, and the electric field was amplified by a high-voltage amplifier and applied to the electrodes. The temperature between the electrodes was set at 43 to 47° C. and maintained constant by a heater with a temperature control apparatus or a peltier element. The humidity was set at 60±10%, and the reaction was carried out in a heat-insulated sealed vessel, a clean environment that suppresses cross-contamination, providing high-quality analysis results.

[ELISA Example]

First, 1 μL of an antigen comprising the allergen was dripped onto a polystyrene or other such plastic substrate, and then the substrate was inserted between parallel plate electrodes having a clearance of 4 mm. A function generator was used to set the electric field fundamental voltage, waveform and frequency, and the electric field was amplified by a high-voltage amplifier and applied to the electrodes. After washing, static blocking was carried out for 30 minutes at 25° C. Similarly, a 1 μL of serum comprising the sample was dripped, and inserted between parallel plate electrodes having a clearance of 4 mm. After washing, 1 μL of peroxidase-labeled secondary antibody was dripped and inserted between parallel plate electrodes having a clearance of 4 mm. After washing, 1 μL of chromogenic substrate solution was added in the presence of 0.1% $H_2O_2$, left standing for 30 minutes at 25° C., and the reaction implemented, shielded from light. These reactions were carried out in a sealed environment at a humidity of 60±10%, in a heat-insulated sealed vessel, a clean environment that suppresses cross-contamination, providing high-quality analysis results.

[Cell Culture Example]

Cells are cultured mainly in petri dishes, test tubes or culture vessels into which the culture solution is placed. In most cases, in the culture process the sample selection and sterilization means are important. Following the seeding, cells merge and proliferate, forming spheroids. Previously monolayer cultures were generally used, but in vivo, cells have a three-dimensional existence, and even ex vivo, cells are said to actively communicate with each other by becoming three-dimensional (forming spheroids). Due to this, culturing spheroids makes it possible to culture cells in a state that is close to in vivo. Following the seeding, cells travel on the plate as they merge and proliferate, growing into spheroids. BT474 (a breast cancer cell strain), for example, requires 5 days to culture by the conventional method. Applying the electric field noncontact stirring method of the present invention enables the culturing to be done expeditiously.

Also, in the case of plants, there is used a culture method (the agarose beads method), in which a protoplast is enclosed in a solid medium (agarose), a liquid medium is added, and the liquid medium part is periodically replaced. 1 g of leaf forming the material is prepared, sterilized, and in a clean bench, is cut into small pieces after removing the veins, subjected to filtration sterilization and processed in an enzyme solution. Enzyme processing time is 2 hours, using a constant-temperature shaker set at 37° C. After the processing, the protoplast is refined by centrifuging it for 3 minutes (at 800 rpm) in a centrifugal separator, and the supernatant is siphoned off, leaving the protoplast precipitate, to which washing liquid is added, followed by centrifuging. This is repeated two times, measured using a Thoma's hemocytometer, and adjusted to a concentration of 104 to 105 cells per milliliter. This conventional method requires two hours of enzyme processing time in a temperature-constant shaker set at 37° C. The processing time can be speeded up by using the noncontact stirring method of the invention to apply a high-voltage alternating-current electric field.

EXAMPLES

In this example, the material of a substrate that immobilizes the probe DNA is preferably a material that exhibits a water-repellent effect with respect to hybridization liquid. (mainly SDS: surfactant, and SSC: sodium chloride and sodium citrate) having a contact angle of at least 45 degrees (a liquid amount of 10 μL at this time).

After the solution is dripped onto a drop region marked on a hydrophilic substrate such as glass using a water-repellent pen, the contact angle of the solution becomes larger than in an unprocessed case. That increases the effect of the electric field noncontact stirring method on the solution, producing vigorous stirring inside the liquid. This makes it possible to achieve a high-quality reaction and an expedited reaction time.

With the conventional stirring method, hybridization was carried out for 10 minutes using a shaker with a constant-temperature bath manufactured by Taitec Company (TAITEC), set at 43 to 47° C. and a humidity of 60±10%.

The following is a detailed explanation, given using examples of the invention.

Example Experiment 1

Example 1

An experiment to confirm the effect of the electric field noncontact stirring method on hybridization was carried out, using the probe DNA immobilized substrate shown in FIG. 1. The probe DNA used was 70 mer long, having a concentration of 5 μM and a drop diameter of approximately 1 mm. The sample DNA was XX type. The substrate was a 25 mm by 75 mm by 1 mm (thick) plastic substrate. 10 μL of a 1:1 mixture of 15 ng/μL or more of a DNA solution and the hybridization liquid that was thermally denatured for 5 minutes at 94° C. followed by rapid cooling to 4° C., was dripped onto the probe DNA immobilization portion. The substrate was inserted between parallel plate electrodes (electrode clearance of 3 mm) in a heat-insulated sealed vessel at 46° C. and a humidity of 60±10%, and a high-voltage alternating-current electric field was applied for 5 minutes. The electric field application conditions set were 32 Hz, 2.6 kV, an offset voltage of 1.7 kV, 16-cycle bursts. After washing with washing liquid and removal of water from the substrate surface, a fluorescent intercalator reagent (5×SYBR Green I) was dripped, left to stand for 5 minutes, and after washing with sterile ultrapure water followed by removal of the water, sterile ultrapure water was further dripped onto the substrate surface, and analysis was carried out using a fluorescence microscope at a beam wavelength of 488 nm.

Figure 4:
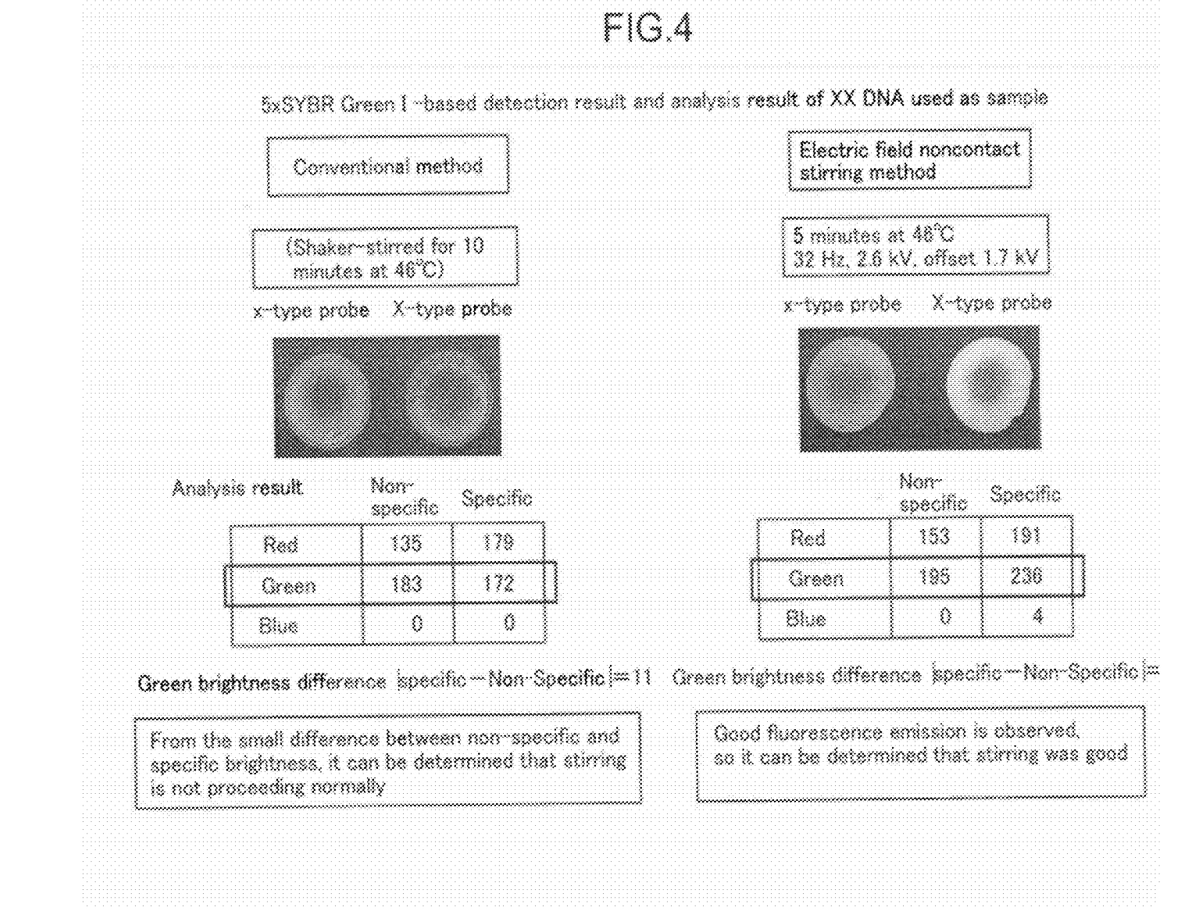
FIG. 4 Photos of detection results in Example Experiment 1, and tables of analysis data obtained therefrom. In the case of the conventional shaker method, specific light-emission was weak, making it difficult to distinguish the genotype, but when electric field noncontact stirring was used, specific light-emission strengthened, making it possible to distinguish the genotype.

The resulting analytical data of the fluorescence color obtained with the fluorescence microscope is shown in FIG. 4. It was possible to quantitatively express the color development results obtained by the fluorescence microscope by a comparison of the three basic colors of the light, Red, Green and Blue, divided into 0 to 255 gradation components. The numerical values of the analysis results obtained showed that compared to when liquid was shaken by a conventional shaker (for 10 minutes at 46° C., with no electric field), the brightness of specific light emission is clearly greater than that of non-specific light emission. Based on that, it is a technology that clearly shows that the electric field noncontact stirring method can manifest high reliability with respect to hybridization reactions.

Example Experiment 2

Example 2

The noncontact stirring behavior of hybridization droplets produced by the application of a high-voltage alternating-current electric field, using the electric field noncontact stirring apparatus shown in FIG. 1, was implemented under a stereoscopic microscope, along with which the behavior of droplets in the case of a conventional noncontact stirring method was observed, as follows.

The experimental conditions were that it was conducted with a 10 μL hybridization droplet containing calcium carbonate (for observation, having a particle diameter of 50 nm and a concentration of 0.05%) in an electric field at 46° C. and a humidity of 60±10% (electrode clearance of 3 mm, 32 Hz, 2.6 kV, offset voltage of 1.7 kV, 16-cycle bursts).

As for the noncontact behavior observation results, there was no movement inside the droplet when there was no electric field, and when an electric field was applied, intense movement of calcium carbonate particles inside the droplet was observed.

Moreover, when, for comparison (Comparative Example 1), as a conventional noncontact stirring method, a shaker with a constant-temperature bath manufactured by Taitec Company (TAITEC) was used to shake a liquid amount of 10 µL for 10 minutes, and a CCD camera was used for observing the motion of the droplet in synch with the motion of the shaker, while there was surface oscillation, no phenomenon of the contents being stirred could be confirmed.

Example Experiment 3

Example 3

Using the electric field noncontact stirring apparatus shown in FIG. 1, the results of analysis of a fluorescent intercalator reagent (5×SYBR Green I) on minute droplets of 10 µL under various hybridization stirring conditions were observed with a fluorescence microscope, using the state of the reaction of sample DNA reacted with probe DNA immobilized on a substrate.

The experiment was carried out at 46° C., for 5 minutes, at 32 Hz, 2.6 kV, an offset voltage of 1.7 kV (electrode clearance of 3 mm), (connected to a −upper electrode and a +lower electrode, 16-cycle bursts), using sample XXDNA. Probe DNA having a length of 70 mer, a concentration of 5 µM and a drop diameter of approximately 1 mm was used.

The analysis results were that the intensity of green fluorescence was low in the case of a non-specific x-type probe state, and the intensity of green fluorescence was high in the case of a specific X-type probe state. From this it was determined that the progress of good hybridization is based on adequate stirring.

Moreover, when, for comparison (Comparative Example 2), as a conventional noncontact stirring method, a similar experiment was conducted in which a shaker with a constant-temperature bath manufactured by Taitec Company was used to shake a liquid amount of 10 µL for 10 minutes at 46° C., it was impossible to tell the difference, confirming the contents could not be stirred.

When, also for comparison (Comparative Example 3), the same electric field noncontact stirring apparatus as in the above Example 2 was used to conduct a similar experiment at 46° C., for 5 minutes, at 110 Hz, 2.6 kV, an offset voltage of 1.7 kV (connected to a −upper electrode and a +lower electrode), it was impossible to tell the difference, confirming the contents could not be stirred.

Example Experiment 4

Example 4

Figure 5:
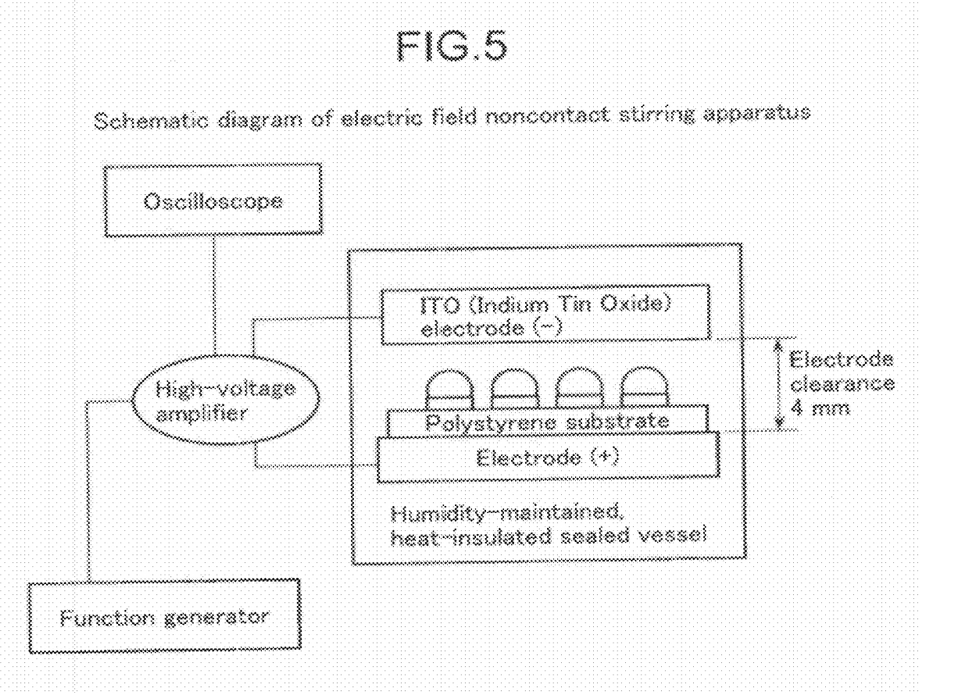
FIG. 5 A cross-sectional drawing showing an outline of the electric field noncontact stirring apparatus used in Example Experiment 4 and Example Experiment 5.
Figure 6:
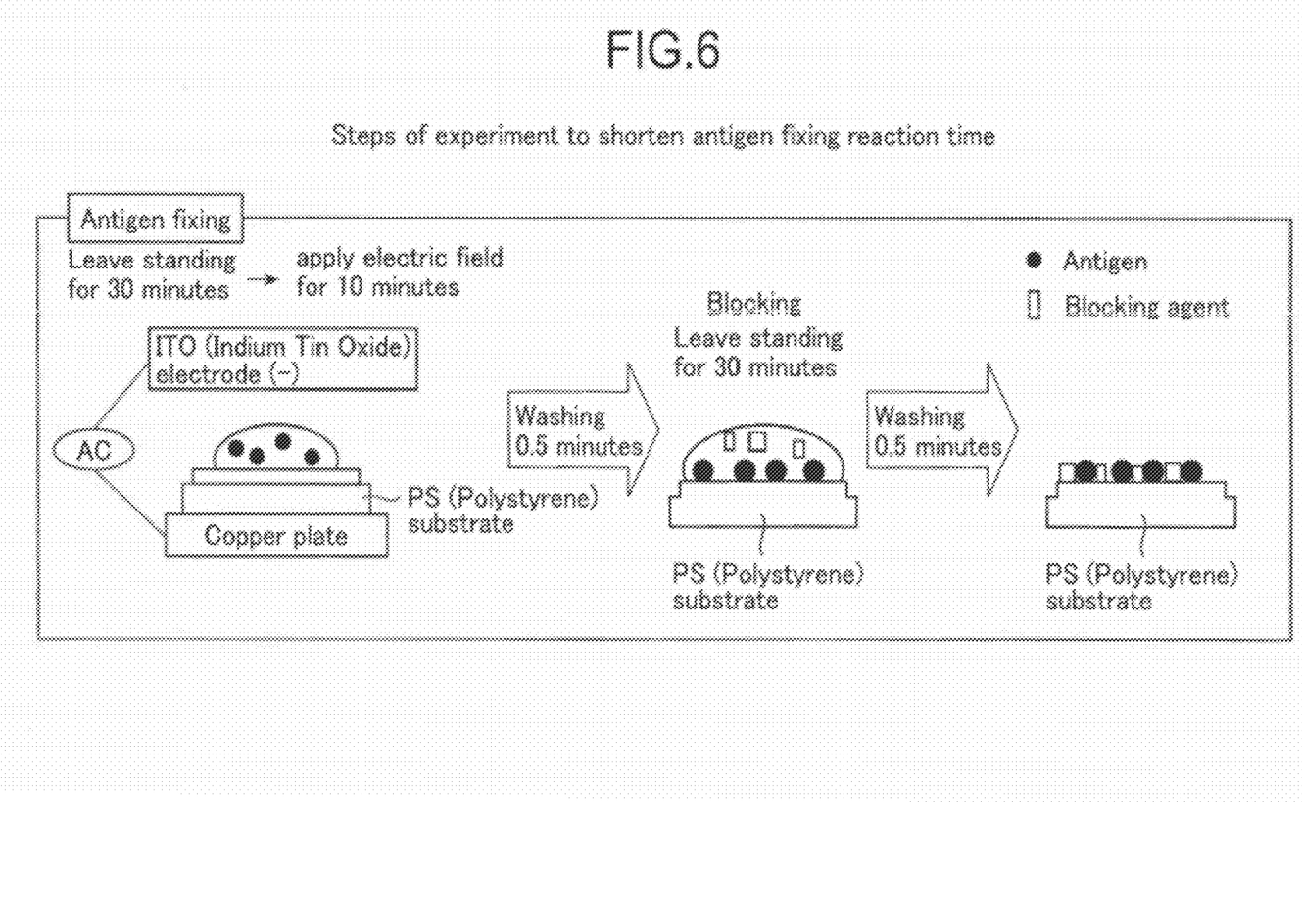
FIG. 6 A drawing showing the steps of Example Experiment 4. Electric field noncontact stirring technology was applied during the antigen fixing reaction.

This was carried out utilizing the effect of an electric field noncontact stirring method with respect to the antigen fixing reaction, using the plastic substrate (polystyrene substrate) shown in FIG. 5 on which antigen solution is dripped. All reactions were carried out in a sealed vessel at 25±2° C. and 60±10%. The experiment processes are shown in FIG. 6.

First, 1 µL of 333 µg/mL of bovine serum albumin (BSA) in PBS was dripped onto the polystyrene substrate. Next, an electric field was applied for 10 minutes, using an electric field noncontact stirring apparatus shown in FIG. 5. Electric field conditions were, 200 Hz, 3 kV, offset voltage of 2 kV (connected to a −upper electrode and a +lower electrode, 3-cycle bursts). Next, after washing with 0.05% Tween 20 in PBS, blocking processing was carried out by leaving it standing for 30 minutes in a solution of 1% egg albumin in PBS. After washing, 1 µL of 1.1 µg/mL anti-BSA antibody in 1% egg albumin solution was dripped and reacted by leaving it standing for 30 minutes. After washing, 1 µL of 3 mM ABTS in 0.1% $H_2O_2$ in a 0.1 M citric acid buffer was dripped, and after standing for 15 minutes, color saturation was measured.

Figure 7:
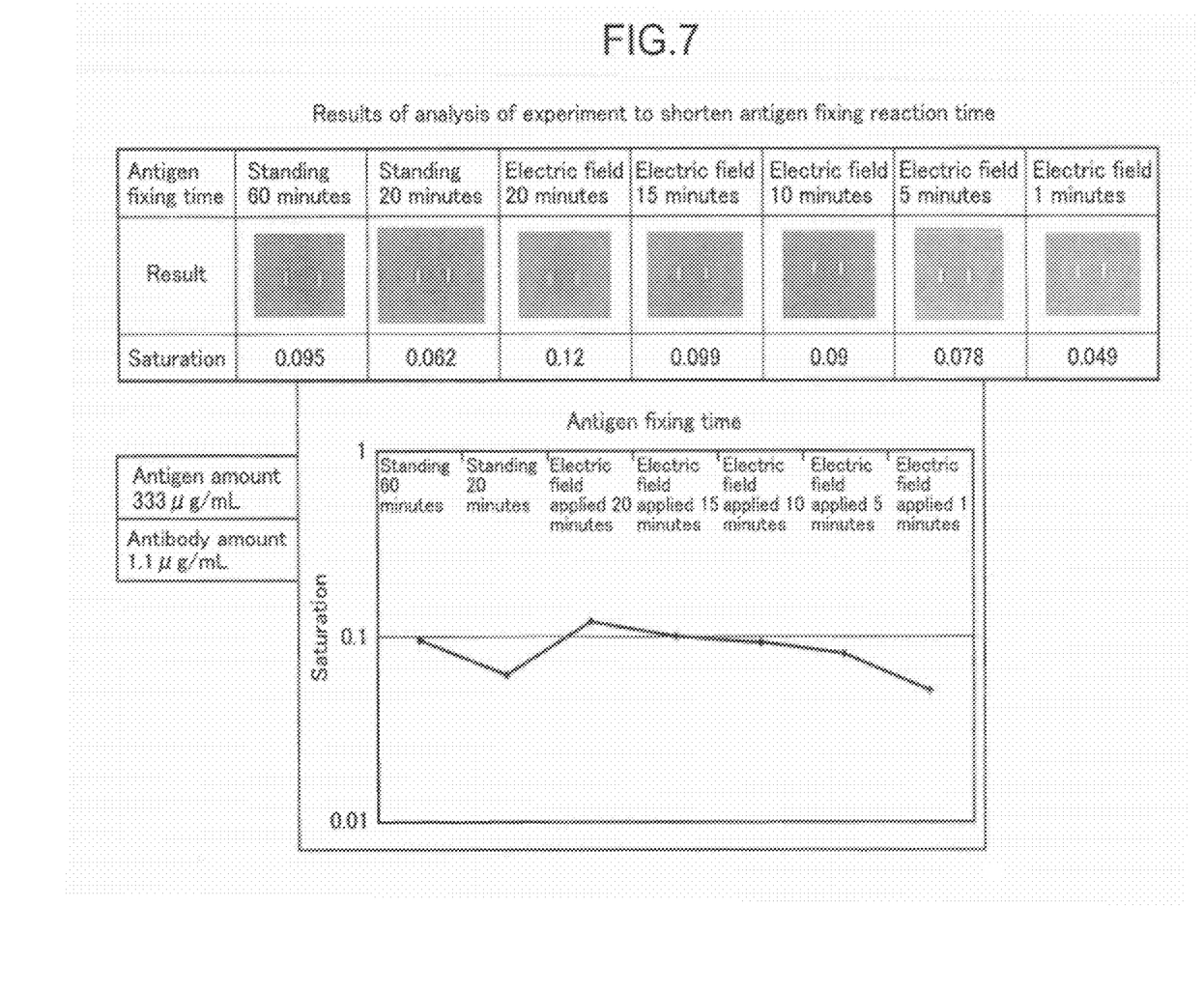
FIG. 7 Photos of analysis results in Example Experiment 4, and a table of analysis data obtained therefrom. Color observed in one-sixth the conventional time, and it was confirmed that by means of electric field noncontact stirring, a good antigen fixing reaction took place in a short time.

As shown in FIG. 7, the analysis results showed that color development was on a par with that of a conventional method, even when the antigen fixing reaction time was 10 minutes. From this, it could be confirmed that the antigen fixing process is energized by the electric field noncontact stirring method, enabling the reaction time to be reduced to one-sixth.

Conjecture relating to the fact that the antigen fixing reaction could be expedited by the electric field noncontact stirring method;

The albumin is 66 kD monomer protein. The size of the albumin is 30 Å (3 nano). From x-ray analysis, it is known that there is unevenness on the molecular surface. The carboxy group (—COO—) of hydrophobic amino acid is electrostatically bound to the hydrophobic plastic that is the substrate by the van der Waals' force. The van der Waals' force works at short distances, so when the electric field noncontact stirring method is used, the stirring effect is manifested in the interior of the minute droplets, and a van der Waals' force acts between the antigen and antibody, efficiently fixing the antigen to the substrate. From this, it is conjectured that good antigen fixing in a short time was made possible by adequate stirring.

Example Experiment 5

Example 5

Figure 8:
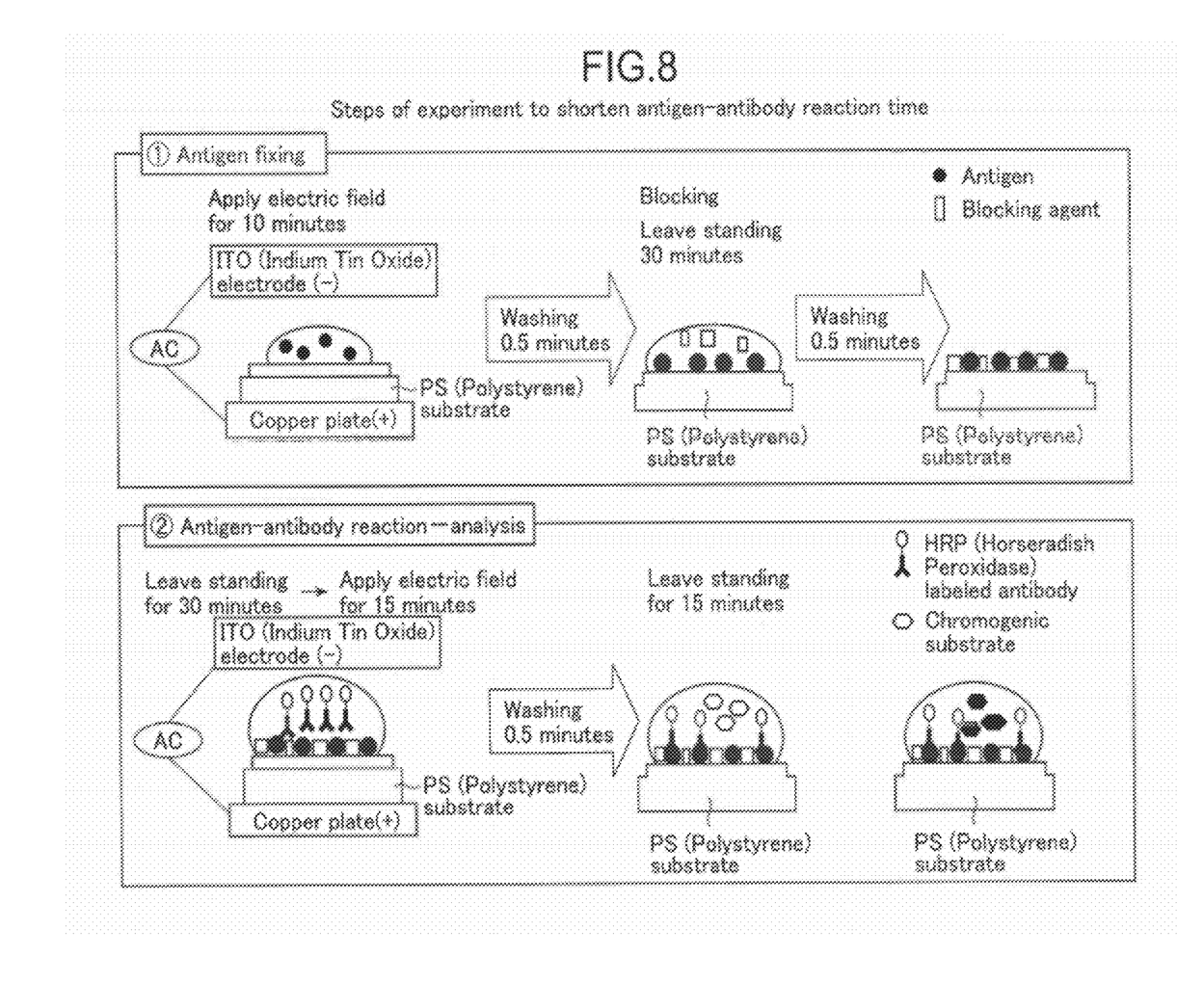
FIG. 8 A drawing showing the steps of Example Experiment 5. Electric field noncontact stirring technology was applied during the antigen fixing reaction and antigen-antibody reaction.

This was carried out utilizing the effect of an electric field noncontact stirring method with respect to the antigen-antibody fixing reaction, using the plastic substrate (polystyrene substrate) shown in FIG. 5 on which 333 µg/mL BSA in PBS solution was fixed. All reactions were carried out in a sealed vessel at 25±2° C. and 60±10%. The experiment processes are shown in FIG. 8.

First, 1 µL of 1.1 µg/mL anti-BSA antibody in 1% egg albumin solution was dripped on the antigen fixing substrate. Next, an electric field was applied for 15 minutes, using the electric field noncontact stirring apparatus shown in FIG. 5. The experiment conditions were the same as those of Example Experiment 4. The washing process, blocking process and color development process were the same as those of Example Experiment 4.

Figure 9:
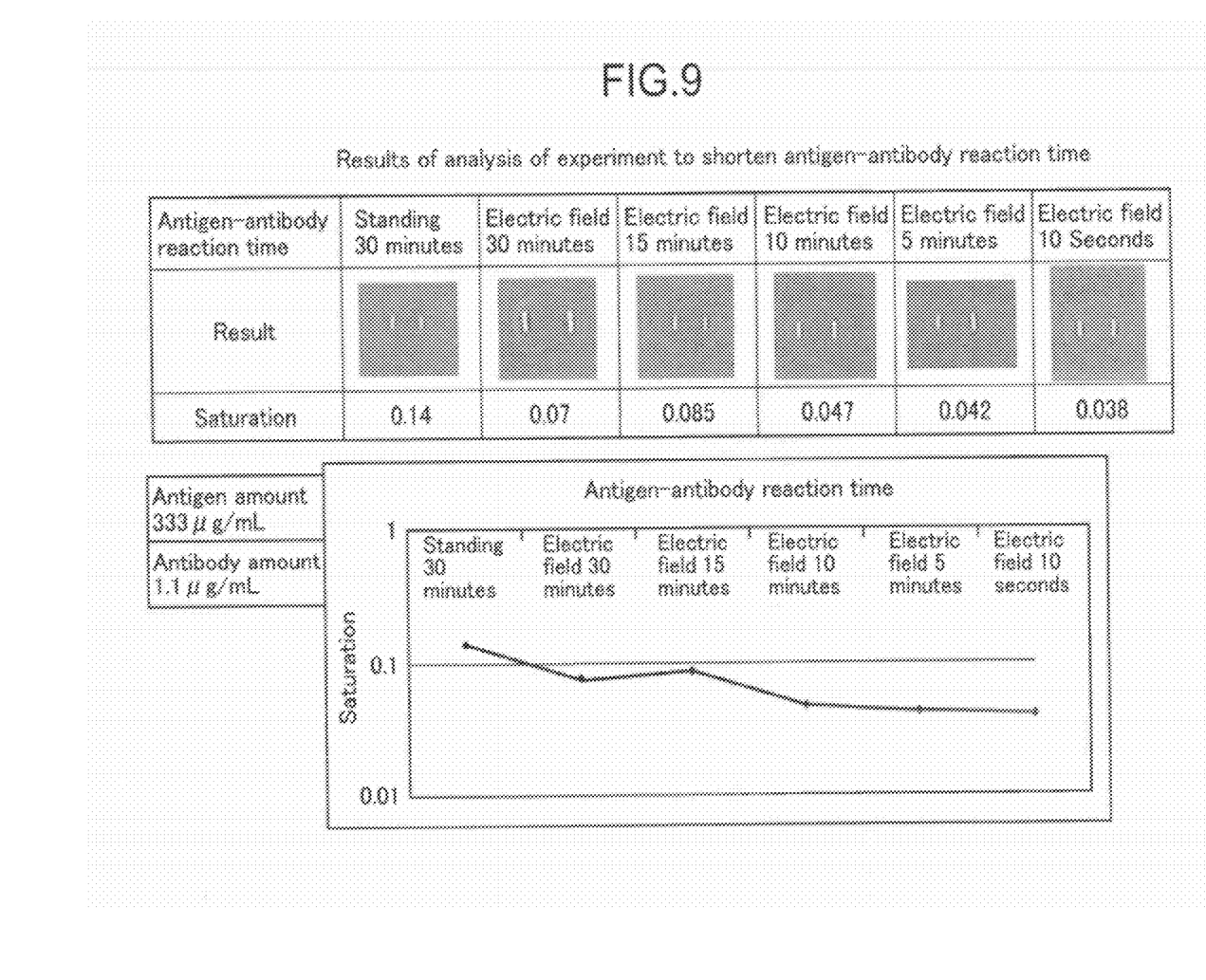
FIG. 9 Photos showing analysis results in Example Experiment 5, and a table of analysis data obtained therefrom. In the antigen-antibody reaction, color observed was observed in one-half the conventional time, and it was confirmed that by means of the electric field noncontact stirring technology, a good antigen-antibody reaction took place. There is an optimum value for the electric field application time: if the application time is too long the bindings are severed, suppressing the normal reaction. In this case 15 minutes was used.

The analysis results were that, as shown in FIG. 9, adequate color development could be confirmed, even in the case of a 15 minute antigen-antibody reaction. Moreover, color development in a short time could not be confirmed. From this, it was possible to confirm that the antigen-antibody reaction time could be halved.

Conjecture relating to the fact that the antigen-antibody reaction was expedited by the electric field noncontact stirring method The antibody binds to the antigen through interactions such as the van der Waals' force, the hydrophobic effect, hydrogen bonding, ion pairs, and so forth. It is known that this binding force is on a par with the affinity of the binding between enzyme and substrate. It is considered that as the van der Waals' force is distance dependent, using an electric field noncontact stirring method gives rise to oscillations within the liquid, and gives rise to molecular collisions, forming an environment that facilitates the action of the van der Waals' force and thereby making it possible to expedite the antigen-antibody reaction.

Figure 10:
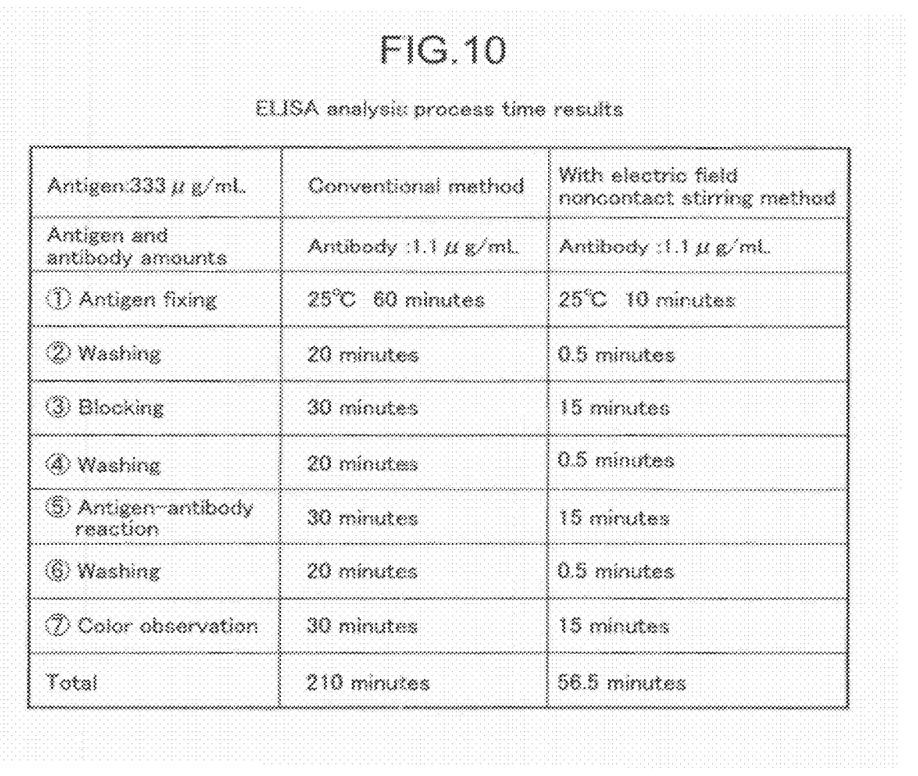
FIG. 10 A table showing the results of the experimental analysis times in Example Experiments 4 and 5.

From this, as shown in FIG. 10, it was confirmed that using the electric field noncontact stirring method made it possible to reduce the ELISA analysis time to one-third.

In the foregoing the present invention has been described based on the embodiment modes of the drawings, but the present invention is not limited to said embodiment modes, and may be carried out in any way that does not change the composition described in the scope of the claims.

What is claimed is:

1. A noncontact stirring method comprising repetitively generating square waves with a plus-side bias having a plus-side main applied voltage of 0.35 to 2.5 kV/mm under a humidity environment of 60±10% by adding an offset voltage of 0.2 to 2.2 kV/mm, applying 2 to 40 frequency bundles of frequency 0.1 to 800 Hz, and applying noncontactively varied electric field waves of a high-voltage alternating-current electric field to minute droplets of 1 mL or less of a liquid solution.

2. A method for a reaction of nucleic acid hybridization, wherein the method comprises the noncontact stirring method of claim 1 for reacting an RNA probe or a DNA probe with a nucleic acid having a complementary RNA sequence or a complementary DNA sequence.

3. A method for detecting nucleic acid in a sample comprising the noncontact stirring method of claim 1, comprising reacting an RNA probe or a DNA probe with a nucleic acid having a complementary RNA sequence or a complementary DNA sequence to obtain a reaction product, dripping a fluorescent intercalator reagent onto the reaction product, and carrying out analysis using a fluorescence microscope.

4. A method for detecting antibodies in a sample, wherein the method comprises the noncontact stirring method of claim 1, comprising fixing a protein serving as an antigen to a plastic substrate, effecting an antigen-antibody reaction using an antibody having a property of binding specifically to said protein serving as the antigen, and utilizing an enzymatic reaction for color development of a chromogenic substrate to detect antibodies.

* * * * *